United States Patent [19]

Keefer et al.

[11] Patent Number: 5,731,305
[45] Date of Patent: Mar. 24, 1998

[54] ANTI-HYPERTENSION COMPOSITIONS OF SECONDARY AMINE-NITRIC OXIDE ADDUCTS AND USE THEREOF

[75] Inventors: Larry Kay Keefer, Bethesda; David Anderson Wink, Hagerstown, both of Md.; Tambra Marie Dunams, Florence, Ala.; Joseph Anthony Hrabie, Frederick, Md.

[73] Assignee: The United States of America as represented by the Department of Health and Human Services, Washington, D.C.

[21] Appl. No.: 476,601

[22] Filed: Jun. 6, 1995

Related U.S. Application Data

[62] Division of Ser. No. 17,270, Feb. 12, 1993, which is a division of Ser. No. 743,892, Aug. 12, 1991, Pat. No. 5,208,233, which is a continuation-in-part of Ser. No. 409,552, Sep. 15, 1989, Pat. No. 5,039,705.

[51] Int. Cl.$^6$ ............................................................ A61K 31/33
[52] U.S. Cl. ............................ 514/183; 540/450; 540/467
[58] Field of Search .......................... 514/183; 540/467, 540/450

[56] References Cited

U.S. PATENT DOCUMENTS

| | | | |
|---|---|---|---|
| 3,153,094 | 10/1964 | Reilly | 260/570 |
| 3,826,832 | 7/1974 | Anderson et al. | 424/250 |
| 4,265,714 | 5/1981 | Nolan et al. | 204/17 |
| 4,482,533 | 11/1984 | Keith | 421/28 |
| 4,638,079 | 1/1987 | Inskip et al. | 560/4 |
| 4,708,854 | 11/1987 | Grinstead | 423/235 |
| 4,921,683 | 5/1990 | Bedell | 423/235 |
| 4,952,289 | 8/1990 | Ciccone et al. | 204/129 |
| 4,954,526 | 9/1990 | Keefer | 514/499 |
| 4,985,471 | 1/1991 | Ohta et al. | 522/27 |
| 5,039,705 | 8/1991 | Keefer et al. | 514/611 |
| 5,087,631 | 2/1992 | Shaffer et al. | 514/342 |
| 5,087,671 | 2/1992 | Loeppky et al. | 525/328.2 |
| 5,094,815 | 3/1992 | Conboy et al. | 422/52 |
| 5,155,137 | 10/1992 | Keefer et al. | 514/611 |
| 5,208,233 | 5/1993 | Keefer et al. | 514/231.8 |
| 5,212,204 | 5/1993 | Keefer et al. | 514/647 |
| 5,234,956 | 8/1993 | Lipton | 514/724 |

FOREIGN PATENT DOCUMENTS

| | | |
|---|---|---|
| 425154 | 10/1990 | European Pat. Off. |
| 211789 | 7/1984 | Germany |
| WO 89/12627 | 6/1989 | WIPO |
| WO 90/09785 | 9/1990 | WIPO |
| WO 91/04022 | 4/1991 | WIPO |
| WO 91/05551 | 5/1991 | WIPO |
| WO 92/05149 | 4/1992 | WIPO |
| WO 93/07114 | 4/1993 | WIPO |
| WO 93/20088 | 10/1993 | WIPO |

OTHER PUBLICATIONS

Adams et al., "Electron–Affinic Sensitization," *Radiation Research*, 67, 9–20 (1976).

Alston et al., "Generation of Nitric Oxide by Enzymatic Oxidation of N-Hydroxy-N-Nitrosamines," *J. Biol. Chem.*, 260 (7), 4069–4074 (1985).

Ames et al., "Uric Acid Provides An Antioxidant Defense in Humans Against Oxidant–And Radical–Caused Aging and Cancer: A Hypothesis," *Proc. Natl. Acad. Sci. USA*, 78, 6858–6862 (1981).

Andrade et al., "Inhibitors of Nitric Oxide Synthase Selectively Reduce Flow in Tumour–Associated Neovasculature," *Br. J. Pharmacol.*, 107, 1092–1095 (1992).

Andrews et al., "Protection Against Gastric Reperfusion Injury by Nitric Oxide: Role of Polymorhophonuclear Leukocytes," *Gastroenterology*, 104, A33 (1993).

Aoki et al., "Beneficial Effects of Two Forms of NO Administration in Feline Splanchnic Artery Occlusion Shock," *Am. J. Physiol.*, 258, G275–G281 (1990).

Artysbasheva et al., "Synthesis of 1–Alkoxy–3,3–Dialkyltriazene 2–Oxides from Alkoxyamines and Nitrosoamines," translated from *Zhurnal Organicheskoi Khimii* (J. Organic Chemistry–U.S.S.R.), 28, (6) 1168–1173 (1987).

Beckman et al., "Apparent Hydroxyl Radical Production by Peroxynitrite: Implications for Endothelial Injury From Nitric Oxide and Superoxide," *Proc. Natl. Acad. Sci. USA*, 87, 1620–1624 (1990).

Beckman, "The Double–Edged Role of Nitric Oxide in Brain Function and Superoxide–Mediated Injury," *J. Developmental Physiol.*, 15, 53–59 (1991).

Beckman, "Ischaemic Injury Mediator," *Nature*, 345, 27–28 (1990).

Bedford et al., "Threshold Hypoxia: Its Effect on the Survival of Mammalian Cells Irradiated at High and Low Dose–Rates," *Br. J. Radiol.*, 39, 896–900 (1966).

(List continued on next page.)

*Primary Examiner*—Shailendra Kumar
*Attorney, Agent, or Firm*—Leydig, Voit & Mayer, Ltd.

[57] ABSTRACT

There are disclosed anti-hypertensive compositions and a method of lowering blood pressure in mammals. The active component in the anti-hypertensive compositions is a compound of the formula

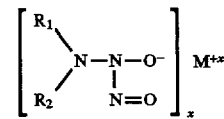

wherein $R_1$ and $R_2$ are independently selected from straight chain and branched chain $C_1$–$C_{12}$ alkyl groups and benzyl, with the proviso that no branch occur on the alpha carbon atom of the alkyl group; or $R_1$ and $R_2$ together with the nitrogen atom they are bonded to form a heterocyclic ring; $M^{+x}$ is a pharmaceutically acceptable cation, wherein x is the valence of the cation.

4 Claims, 2 Drawing Sheets

OTHER PUBLICATIONS

Bohn et al., "Oxygen and Oxidation Promote the Release of Nitric Oxide from Sydnonimines," *J. Cardiovasc. Pharmacol.*, 14, S6–S12 (1989).

Bonakdar et al., "Continuous–Flow Performance of Carbon Electrodes Modified With Immobilized Fe(II)/Fe(III) Centers," *Calanta*, 36, 219–225 (1989).

Coleman et al. "Phase I Trial of the Hypoxic Cell Radiosensitizer SR–2508: The Results of the Five to Six Week Drug Schedule," *Int. J. Radiat. Oncol. Biol. Phys.*, 12, 1105–1108 (1986).

Dawson et al., "Nitric Oxide Synthase and Neuronal NADPH Diaphorase Are Identical in Brain and Peripheral Tissues," *Proc. Natl. Acad. Sci. USA*, 88, 7797–7801 (1991).

DeFeudis, "Endothelium–Dependent Vasorelaxation—A New Basis for Developing Cardiovascular Drugs," *Drugs of Today*, 24 (2), 103–115 (1988).

DeGraff et al., "Evaluation of Nitroimidazole Hypoxic Cell Radiosensitizers in a Human Tumor Cell Line High in Intracellular Glutathione," *I. J. Radiation Oncology Biol. Phys.*, 16, 1021–1024 (1989).

DeLuca et al., "Parenteral Drug–Delivery Systems," in *Pharmaceutics and Pharmacy Practice* (Banker et al., eds.), 238–250 (J.B. Lippincott Co., Philadelphia, PA) (1982).

Drago et al., "The Reaction of Nitrogen(II) Oxide with Various Primary and Secondary Amines," *J. Am. Chem. Soc.*, 83, 1819–1822 (1961).

Drago, "Reactions of Nitrogen(II) Oxide," in *Free Radicals in Organic Chemistry*, Advances in Chemistry Series No. 36, 143–149 (American Chemical Society, Washington, DC) (1962).

Fast et al., "Nitric Oxide Production by Tumor Targets in Response to TNF: Paradoxical Correlation With Susceptibility to TNF–Mediated Cytotoxicity Without Direct Involvement in the Cytotoxic Mechanism," *J. Leukocyte Biol.*, 52, 255–261 (1992).

Feelisch et al., "On the Mechanism of NO Release from Sydnonimines," *J. Cardiovasc. Pharmacol.*, 14, S13–S22 (1989).

Feelisch, "The Biochemical Pathways of Nitric Oxide Formation from Nitrovasodilators: Appropriate Choice of Exogenous NO Donors and Aspects of Preparation and Handling of Aqueous NO Solutions," *J. Cardiovasc. Pharmacol.*, 17, S25–S33 (1991).

Filep et al., "Nitric Oxide Modulates Vascular Permeability in the Rat Coronary Circulation," *Br. J. Pharmacol.*, 108, 323–326 (1993).

Fujitsuka et al., "Nitrosohydroxylamines," *Chem. Abstracts*, 82, 31108P (1975).

Furchgott, "The Role of Endothelium in the Responses of Vascular Smooth Muscle to Drugs," *Ann. Rev. Pharmacol. Toxicol.*, 24, 175–97 (1984).

Gambassi et al., "Ischemia–Reperfusion Injury and Histamine Release in Isolated Perfused Guinea–Pig Heart: Effects of Nitric Oxide Generators," *Pharmacological Research*, 26, 11–12 (1992).

Garg et al., "Nitric Oxide–Generating Vasodilators Inhibit Mitogenesis and Proliferation of Balb/C3T3 Fibroblasts By A Cylic GMP–Independent Mechanism," *Biochem. and Biophys. Res. Comm.*, 171, 474–479 (1990).

Gatenby et al., "Oxygen Distribution in Squamous Cell Carcinoma Metastases and its Relationship to Outcome of Radiation Therapy," *I. J. Radiation Oncology Biol. Phys.*, 14, 831–838 (1988).

Gehlen et al., "Über Reaktionen und Eigenschaften des Stickoxyds und seiner Verbindungen (II. Mitteil): Zur Kenntnis der Salze der Stickoxyd–schwefligen Säure," *Berichte d. D. Chem. Gesellschaft*, LXV, 1130–1140 (1932). (Reactions and properties of nitric oxide and its compounds. II. The salts of the nitric oxide compound of sulfurous acid, *Chemical Abstracts*, 26, 4764–65.).

Gelvan et al., "Cardiac Reperfusion Damage Prevented by a Nitroxide Free Radical," *Proc. Natl Acad. Sci. USA*, 88, 4680–4684 (1991).

Granger, "Role of Xanthine Oxidase and Granulocytes in Ischemia–Reperfusion Injury," *Am. J. Physiol.*, 255, H1269–H1275 (1988).

Hall, "The Oxygen Effect and Reoxygenation, in Radiobiology for the Radiologist" (4th ed.), 133–164 (J.P. Lippincott Co. Philadelphia) (1994).

Hall et al., "Extreme Hypoxia; Its Effect on the Survival of Mammalian Cells Irradiated at High and Low Dose–Rates," *Br. J. Radiol.*, 39, 302–307 (1966).

Halliwell et al., "Oxygen Toxicity, Oxygen Radicals, Transition Metals and Disease," *Biochem. J.*, 219, 1–14 (1984).

Halliwell et al., "Biologically Relevant Metal Ion–Dependent Hydroxyl Radical Generation," *FEBS*, 307, 108–112 (1992).

Halliwell et al., "Oxygen Free Radicals and Iron in Relation to Biology and Medicine: Some Problems and Concepts," *Arch. Biochem. and Biophys.*, 246, 501–514 (1986).

Hanbauer et al., "Role of Nitric Oxide in NMDA–Evoked Release of [$^3$H]–Dopamine From Striatal Slices," *Neuroreport*, 3, 409–412 (1992).

Hansen et al., "N–Nitrosation of Secondary Amines by Nitric Oxide via the 'Drago Complex'," in *N–Nitroso Compounds: Occurrence and Biological Effects*, IARC Scientific Publications No. 41, 21–29 (International Agency for Research on Cancer, Lyon, France) (1982).

Hibbs et al., "Nitric Oxide: A Cytotoxic Activated Macrophage Effector Molecule," *Biochem. and Biophys. Res. Comm.*, 157, 87–94 (1988).

Holford et al., "Understanding the Dose–Effect Relationship: Clinical Application of Pharmacokinetic–Pharmacodynamic Models," *Clinical Pharmacokinetics*, 429–453 (1981).

Howard–Flanders, "Effect of Nitric Oxide on the Radiosensitivity of Bacteria," *Nature*, 180, 1991–1192 (1957).

Hrabie et al., "New Nitric Oxide–Releasing Zwitterions Derived from Polyamines," *J. Org. Chem.*, 58, 1472–1476 (1993).

Hutcheson et al., "Role of Nitric Oxide in Maintaining Vascular Integrity in Endotoxin–Induced Acute Intestinal Damage in the Rat," *Br. J. Pharmacol.*, 101, 815–820 (1990).

Ignarro et al., "Mechanism of Vascular Smooth Muscle Relaxation by Organic Nitrates, Nitrites, Nitroprusside and Nitric Oxide: Evidence for the Involvement of S–Nitrosothiols as Active Intermediates," *J. Pharmacol. Exp. Ther.*, 218, 739–749 (1981).

Ignarro, "Endothelium–derived nitric oxide: actions and Properties," *The FASEB Journal*, 3, 31–36 (1989).

Ignarro, "Biosynthesis and Metabolism of Endothelium–Derived Nitric Oxide," *Ann. Rev. Pharmacol. Toxicol.*, 30, 535–60 (1990).

Ignarro et al., "The Pharmacological and Physiological Role of Cyclic GMP in Vascular Smooth Muscle Relaxation," *Ann. Rev. Pharmacol. Toxicol.*, 25, 171–191 (1985).

Ignarro, "Nitric Oxide: A Novel Signal Transduction Mechanism for Transcellular Communication," *Hypertension*, 16, 477–483 (1990).

Imlay et al., "Toxic DNA Damage by Hydrogen Peroxide Through the Fenton Reaction in vivo and in vitro," *Science*, 240, 640–642 (1988).

Ischiropoulos et al., "Peroxynitrite–Mediated Tyrosine Nitration Catalyzed by Superoxide Dismutase," *Arch. Biochem. and Biophys.*, 298, 431–437 (1992).

Jaeschke et al., "Role of Nitric Oxide in the Oxidant Stress During Ischemia/Reperfusion Injury of the Liver," *Life Sciences*, 50, 1797–1804 (1992).

Johnson et al., "Cardioprotective Effects of Authentic Nitric Oxide in Myocardial Ischemia With Reperfusion," *Critical Care Medicine*, 19, 244–252 (1991).

Jones, "Metastable Polymers of the Nitrogen Oxides. 1. Open Chain Nitric Oxide Analogues of Polythiazyl: ANN DO/AM1 Study," *J. Phys. Chem.*, 95, 2588–2595 (1991).

Kanner et al., "Nitric Oxide as an Antioxidant," *Archives of Biochemistry and Biophysics*, 289, 130–136 (1991).

Keefer et al "Complexes of Nitric Oxide with Nucleophiles as Agents for the Controlled Biological Release of Nitric Oxide," *Biology of Nitric Oxide, 2, Enzymology, Biochemistry, Immunology*, (Moncada et al., eds.), 153–156 (Portland Press, Chapel Hill, NC) (1992).

Kiedrowski et al., "Sodium Nitroprusside Inhibits N–Methyl–D–aspartate–Evoked Calcium Influx via a Nitric Oxide– and cGMP–Independent Mechanism," *Molecular Pharmacology*, 41, 779–784 (1992).

Kruszyna et al., "Red Blood Cells Generate Nitric Oxide from Directly Acting, Nitrogenous Vasodilators," *Toxicol. Appl. Pharmacol.*, 91, 429–438 (1987).

Kubes et al., "Nitric Oxide Modulates Microvascular Permeability," *Am. J. Physiol.*, 262, H611–H615 (1992).

Kubes et al., "Nitric Oxide: An endogenous Modulator of Leukocyte Adhesion," *Proc. Natl. Acad. Sci. USA*, 88, 4651–4655 (1991).

Kubes et al., "Nitric Oxide Protects Against Ischemia/ Reperfusion–Induced Mucosal Dysfunction," *Gastroenterology*, 104, A728 (1993).

Kuhn et al., "Endothelium–Dependent Vasodilatation in Human Epicardial Coronary Arteries: Effect of Prolonged Exposure to Glycerol Trinitrate or SIN–1," *J. Cardiovasc. Pharmacol.*, (Suppl. 11), S47–S54 (1989).

Kuznetsov et al., "Photoelectron spectra and electronic structures of 2–alkoxy–1–tert–alkydiazen–1–oxides and 1–alkoxy–3,3–dialkyltriazen–2–oxides," *J. Mol. Struct.*, 263, 329–341 (1991).

Kwon et al., "Inhibition of Tumor Cell Ribonucleotide Reductase by Macrophage–Derived Nitric Oxide," *J. Exp. Med.*, 174 (4) 761–767 (1991).

Lafon–Cazal et al., "NMDA–Dependent Superoxide Production and Neurotoxicity," *Nature*, 364, 535–537 (1993).

Lefer et al., "Pharmacology of the Endothelium in Ischemia–Reperfusion and Circulatory Shock," *Ann. Rev. Pharmacol. Toxicol.*, 33, 71–90 (1993).

Linz et al., "ACE–Inhibition Induces NO–Formation in Cultured Bovine Endothelial Cells and Protects Isolated Ischemic Rat Hearts," *J. Mol. Cell Cardiol.*, 24, 909–919 (1992).

Lipton et al., "A Redox–Based Mechanism for the Neuroprotective and Neurodestructive Effects of Nitric Oxide and Related Nitroso–Compounds," *Nature*, 364, 626–631 (1993).

Longhi et al., "Metal–Containing Compounds of the Anion $(C_2H_5)_2NN_2O_2^-$," *Inorg. Chem.*, 2, 85–88 (1963).

Lutz et al., "Isolation of Trioxodinitrato(II) Complexes of Some First Row Transition Metal Ions," *J.C.S. Chem. Comm.*, 247 (1977).

Maragos et al., "Complexes of •NO with Nucleophiles as Agents for the Controlled Biological Release of Nitric Oxide. Vasorelaxant Effects," *J. Med. Chem.*, 34, 3242–3247 (1991).

Maragos et al., "Nitric Oxide/Nucleophile Complexes Inhibit the in vitro Proliferation of A375 Melanoma Cells via Nitric Oxide Release," *Cancer Res.*, 53 (3), 564–568 (1993).

Marletta et al., "Unraveling the Biological Significance of Nitric Oxide," *BioFactors*, 2, 219–225 (1990).

Marmo et al., "Cardiovascular and Respiratory Effects of Spermidine and Spermine: An Experimental Study," *Biomed. Biochim. Acta*, 43, 509–515 (1984).

Masini et al., "Effect of Nitric Oxide Generators on Ischemia–Reperfusion Injury and Histamine Release in Isolated Perfused Guinea Pig Heart," *Int. Arch. Allergy Appl. Immunol*, 94, 257–258 (1991).

Masini et al., "The Effect of Nitric Oxide Generators on Ischemia Reperfusion Injury and Histamine Release in Isolated Perfused Guinea–Pig Heart," *Agents and Actions*, 33, 53–56 (1991).

Middleton et al., "Further Studies on the Interaction of Nitric Oxide With Transition–Metal Alkyls," *J. Chem. Soc. Dalton*, 1898–1905, (1981).

Minotti et al., "The Requirement for Iron (III) in the Initiation of Lipid Peroxidation by Iron (II) and Hydrogen Peroxide," *J. Biol. Chem.*, 262, 1098–1004 (1987).

Mitchell et al., "Biologically Active Metal–Independent Superoxide Dismutase Mimics," *Biochemistry*, 29, 2802–2807 (1990).

Mitchell et al., "Cellular Glutathione Depletion by Diethyl Maleate or Buthionine Sulfoximine: No Effect of Glutathione Depletion on the Oxygen Enhancement Ratio," *Radiation Research*, 96, 422–428 (1983).

Morikawa et al., "L–Arginine Decreases Infarct Size Caused by Middle Cerebral Arterial Occlusion in SHR," *Am. J. Physiol.*, 263, H1632–H1635 (1992).

Morley et al., "Mechanism of Vascular Relaxation Induced by the Nitric Oxide (NO)/Nucleophile Complexes, a New Class of NO–Based Vasodilators," *J. Cardiovasc. Pharmacol.*, 21, 670–676 (1993).

Murad et al., Propr. Clin. Biol. Res., 249, 65–76 (1983).

Murayama et al., "Radiosensitization of Hypoxic HeLa S3 Cells in vitro by a New Type of Radiosensitizer: Spermine and Spermidine Amides with Nitro Groups," *Int. J. Radiat. Biol.*, 44, 497–503 (1983).

Myers et al., "Vasorelaxant properties of the endothelium–derived relaxing factor more closely resemble S–nitrosocystein than nitric oxide," *Nature*, 345, 161–163 (1990).

Palmer et al., "Nitric oxide release accounts for the biological activity of endothelium–derived relaxing factor," *Nature*, 327, 324–327 (1987).

Park et al., "Controlled Protein Release from Polyethyleneimine–Coated Poly(L–lactic Acid)/Pluronic Blend Matrices," *Pharmaceut. Res.*, 2, 37–39 (1992).

Phillips et al., "Variation in Sensitizing Efficiency for SR 2508 In Human Cells Dependent on Glutathione Content," *I. J. Radiation Oncology Biol. Phys.*, 12, 1627–1635 (1986).

Phillips et al., "Promise of Radiosensitizers and Radioprotectors in the Treatment of Human Cancer," *Cancer Treatment Reports*, 68, 291–302 (1984).

Powers et al., "A Multicomponent X-Ray Survival Curve for Mouse Lymphosarcoma Cells Irradiated in vivo," *Nature*, 197, 710–711 (1963).

Radi et al., "Peroxynitrite–Induced Membrane Lipid Peroxidation: The Cytotoxic Potential of Superoxide and Nitric Oxide," *Arch. Biochem. and Biophys.*, 288, 481–487 (1991).

Radomski et al., "Endogenous Nitric Oxide Inhibits Human Platelet Adhesion to Vascular Endothelium," *The Lancet*, 1057–1058 (1987).

Rapoport et al., *Protein Phosph. Research*, S (4–5), 281–296 (1983).

Rubanyi et al., "Cytoprotective Function of Nitric Oxide: Inactivation of Superoxide Radicals Produced by Human Leukocytes," *Biochem. and Biophys. Res. Comm.*, 181, 1392–1397 (1991).

Russo et al., "The Effects of Cellular Glutathione Elevation on the Oxygen Enhancement Ratio," *Radiation Research*, 103, 232–239 (1985).

Saavedra et al., "Secondary Amine/Nitric Oxide Complex Ions, $R_2N[N(O)NO^-]$ O–Functionalized Chemistry," *J. Org. Chem.*, 57, 6134–138 (1992).

Saran et al., "Reaction of NO With $O_2-$. Implications for the Action of Endothelium–Derived Relaxing Factor (EDRF)," *Free Rad. Res. Comm.*, 10, 221–226 (1990).

Siegfried et al., "Beneficial effects of SPM–5185, a cysteine–containing NO donor in myocardial ischemia–reperfusion," *Am. J. Physiol.*, 263, H771–H777 (1992).

Siegfried et al., "Cardioprotection and Attenuation of Endothelial Dysfunction by Organic Nitric Oxide Donors in Myocardial Ischemia–Reperfusion," *J. Pharmacol. and Exp. Therapeutics*, 260, 668–675 (1992).

Siemann et al. "Characterization of Radiation Resistant Hypoxic Cell Subpopulations In KHT Sarcomas. (ii) Cell Sorting," *Br. J. Cancer*, 58, 296–300 (1988).

Smith et al., "Nitroprusside: A Potpourri of Biologically Reactive Intermediates," in *Advances in Experimental Medicine and Biology, 283, Biological Reactive Intermediates IV* (Witmer et al., eds.), 365–369 (Plenum Press, New York, NY) (1991).

Smith et al., "Complex Contractile Patterns in Canine Colon Produced by Spontaneous Release of Nitric Oxide," *Gastroenterology*, 102 (Part 2), A516 (1992).

Stamler et al., "S–Nitrosylation of proteins with nitric oxide: Synthesis and characterization of biologically active compounds," *Proc. Natl. Acad. Sci. USA*, 89, 444–448 (1992).

Stamler et al., "Nitric Oxide Circulates in Mammalian Plasma Primarily as an S–Nitroso Adduct of Serum Albumin," *Proc. Natl. Acad. Sci. USA*, 89, 7674–7677 (1992).

Stuehr et al., "Nitric Oxide: A Macrophage Product Responsible for Cytostasis and Respiratory Inhibition in Tumor Target Cells," *J. Exp. Med.*, 169, 1543–1555 (1989).

Thomlinson et al., "The Histological Structure of Some Human Lung Cancers and the Possible Implications for Radiotherapy," *Br. J. Cancer*, IX, 539–549 (1955).

Trissel, "Intravenous Infusion Solutions," *Handbook on Injectable Drugs* (4th ed.), 622–629 (American Society of Hospital Pharmacists, Bethesda, MD) (1986).

von Sonntag, *The Chemical Basis of Radiation Biology*, pp. 31–56 and 295–352 (Taylor & Francis, London) (1987).

Weitz et al., "Zur Kenntnis der stickoxyd–schwefligen Säure (II.Mitteil)," *Berichte d. D. Chem. Gesellschaft*, LXVI, 1718–1727 (1933). (Nitrosylsulfuric acid, *Chemical Abstracts*, 28, 2636.).

WHO Task Group on Environmental Health Criteria for Oxides of Nitrogen, *Environmental Health Criteria 4: Oxides of Nitrogen*, (World Health Organization, Geneva) (1977).

Wiersdorff et al., "N–aryl–N–nitrosohydroxylamine salts," *Chem. Abstracts*, 77, 48034f (1972).

Wilcox et al., "Effect of Cyanide on the Reaction of Nitroprusside with Hemoglobin: Relevance to Cyanide Interference With the Biological Activity of Nitroprusside," *Chem. Res. Toxicol.*, 3, 71–76 (1990).

Wink et al., "DNA Deaminating Ability and Genotoxicity of Nitric Oxide and Its Progenitors," *Science*, 254, 1001–1003 (1991).

Woditsch et al., "Prostacyclin Rather Than Endogenous Nitric Oxide is a Tissue Protective Factor in Myocardial Ischemia," *Am. J. Physiol.*, 263, H1390–H1396 (1992).

Wood et al., "Modification of Energy Metabolism and Radiation Response of A Murine Tumour by Changes in Nitric Oxide Availability," *Biochem. and Biophys. Res. Comm.*, 192, 505–510 (1993).

Zhu et al., "Bactericidal Activity of Peroxynitrite," *Arch. of Biochem. and Biophy.*, 298, 452–457 (1992).

ANTI-HYPERTENSION COMPOSITIONS OF SECONDARY AMINE-NITRIC OXIDE ADDUCTS AND USE THEREOF

This is a divisional of copending application(s) Ser. No. 08/017,270, filed on Feb. 12, 1993, which, in turn, is a divisional of application Ser. No. 07/743,892, filed on Aug. 12, 1991, now U.S. Pat. No. 5,208,233, which is, in turn, a continuation-in-part of application Ser. No. 07/409,552, filed on Sep. 15, 1989, now U.S. Pat. No. 5,039,705.

FIELD OF THE INVENTION

The present invention relates to novel pharmaceutical compositions and to a method of treating hypertension. Related compositions and methods are described in U.S. Pat. No. 4,954,526, issued Sep. 4, 1990 and U.S. patent application Ser. No. 07/423,279, filed on Oct. 18, 1989 and in U.S. patent application Ser. No. 07/585,793, filed on Sep. 20, 1990, each of which is incorporated herein by reference in its entirety.

BACKGROUND OF THE INVENTION

Endothelium-derived relaxing factor (EDRF) is a labile humoral agent which is part of a cascade of interacting agents involved in the relaxation of vascular smooth muscle. EDRF is thus important in the control of vascular resistance to blood flow and in the control of blood pressure. Some vasodilators act by causing EDRF to be released from endothelial cells. (See Furchgott, Ann. Rev. Pharmacol. Toxicol. 24, 175–197, 1984.) Recently, Palmer et al., have shown that EDRF is identical to the simple molecule, nitric oxide, NO (Nature 317, 524–526, 1987). It has been hypothesized for years that many nitrovasodilators that mimic the effect of EDRF, like glyceryl trinitrate, amyl nitrite, $NaNO_2$ and sodium nitroprusside (SNP), do so by virtue of their conversion to a common moiety, namely NO, which is also a vasodilator. (See Kruszyna et al., Tox.& Appl. Pharmacol., 91, 429–438, 1987; Ignarro, FASEB J. 3, 31–36, 1989 and Ignarro et al., J. Pharmacol. Exper. Theraputics 218(3), 739–749, 1981.)

SUMMARY OF THE INVENTION

It has now been discovered that certain compounds encompassed by the structure:

wherein A is a secondary amino group, $M^{+x}$ is a pharmaceutically acceptable cation and x is the valence of the cation, are potent anti-hypertensives and thus are useful for treating cardiovascular disorders in which lowering the blood pressure has a beneficial result. It is believed that these compounds function by releasing NO in the blood after injection; however the invention should not be limited by this hypothesis. These compounds are for the most part known. However, there is no suggestion in the previous literature that they are anti-hypertensive, indeed, there is no suggestion in the previous art that these compounds have any pharmaceutical use. Nonetheless, some of the compounds are described by Drago in "Free Radicals in Inorganic Chemistry", Number 36, Advances in Chemistry Series, American Chemical Society, Wash. DC, 1962, pages 143–149 and by Drago et al, J. Amer. Chem. Soc. 83, 1819–1822, 1961. These two articles by Drago are incorporated herein by reference, in their entirety. The two Drago references mention no utility for the compounds whatsoever. Similarly, Reilly, in U.S. Pat. No. 3,153,094, also discloses some of these compounds at columns 11–13 thereof, but does not teach any biological activity thereof.

BRIEF DESCRIPTION OF THE DRAWINGS

The present invention will become more fully understood from the detailed description given here and below and the accompanying drawings which are given by way of illustration only, and thus, are not limitative of the present invention, and wherein.

▲=Bis(piperidino)bis(nitric oxide) Adduct of Example 2 (mean).

○=glyceryl trinitrate (mean).

●=sodium nitroprusside (mean).

Δ=Bis(morpholino)bis(nitric oxide) adduct of Example 3 (mean).

○=glyceryl trinitrate (mean).

⊚=sodium nitroprusside (mean).

DETAILED DESCRIPTION OF THE INVENTION

The present invention provides pharmaceutical compositions comprising: a compound of the following formula I wherein $R_1$ and $R_2$ are independently selected from straight chain and branched chain alkyl groups of one to twelve carbon atoms or benzyl, with the proviso that no branch occur on the alpha carbon of the alkyl groups, or $R_1$ and $R_2$ together with the nitrogen atom they are bonded to form a heterocyclic group, preferably selected from the group consisting of wherein w is 1 to 12, y is 1 or 2, z is 1 to 5, $R_7$ is hydrogen, $C_{1-8}$ straight chain alkyl, $C_{3-6}$ branched chain alkyl, $C_{3-8}$ cycloalkyl, phenyl or tolyl, and $R_8$ is hydrogen, $C_{1-6}$ straight chain alkyl or $C_{3-6}$ branched chain alkyl; $M^{+x}$ is a pharmaceutically acceptable cation, wherein x is the valence of the cation (its charge); and a pharmaceutically acceptable carrier. By straight chain alkyl is meant the non-branched methyl, ethyl, n-propyl, n-butyl, n-decyl, and like groups. By branched chain alkyl is meant groups like 3-methylpentyl, 2-methylpropyl, and the like. The proviso means that groups like isopropyl or 1-methylbutyl are excluded. The $C_1$ to $C_6$ alkyls are preferred. Of the $R_1R_2N$—heterocyclic groups encompassed thereby, there are mentioned, for example, azetidino, pyrrolidino, piperidino, azacylooctane, substituted piperidino (e.g. 2-methyl, 3-methyl, 4-methyl, 2-ethyl, 4-phenyl, 2-propyl, 4-propyl and 4-tert.butylpiperidino), substituted pyrrolidino (e.g., 2-methyl and 3-methylpyrrolidino), 1,2,3,6-tetrahydropyridino, 3-pyrrolino, morpholino, hexamethyleneimino, 1-aza-12-crown-4, 1-aza-15-crown-5 and 1-aza-18-crown-6. Morpholino is a preferred $R_1R_2N$—moiety. Many commercially available nitrogen-containing heterocyclic compounds can be used to prepare compounds of Formula I wherein $R_1R_2N$— is a heterocyclic moiety. For example, such compounds can be obtained from the chemical companies of: Aldrich; American Tokyo Kasei, Inc.; Reilly Industries, Inc.; and Pfaltz and Bauer.

By a pharmaceutically acceptable cation is meant any non-toxic cation; these are well known to one of ordinary skill in the art. The cation should not render the compound unstable or insoluble in water. Generally the cation will be a group 1 or group 2 cation, such as sodium, potassium, magnesium or calcium ions, or $NR_3R_4R_5R_6^+$, wherein $R_3$, $R_4$, $R_5$, and $R_6$ are independently chosen from H, $C_1$–$C_{12}$ alkyl, $C_3$–$C_7$ cycloalkyl or benzyl, more preferably H, $C_1$–$C_4$ alkyl or $C_6$ cycloalkyl. The method of synthesis discussed below first results in the cation being $R_1R_2H_2N^+$, these cations work well. The most preferred cations are $Na^+$, $K^+$, $Ca^{+2}$, and $R_1R_2H_2N^+$.

The compositions are potent anti-hypertensives. They are useful for lowering the blood pressure and treating any cardiovascular disorder in which lowering the blood pressure will have a beneficial effect. The invention provides an effective method of lowering the blood pressure by administering the composition to a mammal.

The methods of synthesis are the same as disclosed by Drago et al., J. Amer. Chem. Soc., 83, 1819–1822, 1961. Generally, the secondary amine ($R_1R_2HN$) is dissolved in anhydrous ether, oxygen is removed from the system, the temperature is lowered to −78° C., and dry NO is bubbled through the ether solution. The reaction can be run at high pressure (100 psi) or at atmospheric pressure. The same product is obtained, but the yields are higher using the high pressure method. The same methodology is used to make all the compounds, with the only principal difference being the starting secondary amine. Examples 1a and 1b give the details of how the diethylamine complex was made, while Examples 2–4 describe the preparation of secondary heterocyclic amine-nitric oxide complexes.

EXAMPLE 1a

Preparation of Bis(diethylamino)bis(nitric Oxide) Adduct

Anhydrous diethylamine (100 ml) was dissolved in 100 ml of anhydrous diethyl ether and was placed in a three-necked flask. Two of the necks served as inlets for $N_2$ and NO, and the third was an outlet. The flask was flushed with $N_2$ and the mixture cooled to −78° C. using an acetone-dry ice bath. Commercial grade NO was bubbled through 10M NaOH and dried by passing it through a column containing NaOH pellets, and then bubbled for 3 hr through the diethylamine/diethyl ether solution. The mixture was allowed to warm to room temperature overnight (18 hr). The product precipitated from solution. The product was filtered and washed with diethyl ether. Three grams (3% yield) of crude product was obtained. The product was purified by suspending it in diethyl ether, adding sufficient neutralized chloroform dropwise to just dissolve the product, and placing the mixture in the freezer. The resultant crystals were then filtered, washed with diethyl ether and dried by vacuum.

$^1$H NMR (200 MHz): 3.07 (q, 4H, J=7.2 Hz), 2.94 (q, 4H, J=7.2 Hz), 1.27 (t, 6H, J=7.2 Hz), 0.96 (t, 6H, J=7.2 Hz). $^{13}$C NMR (50 MHz): 51.3, 45.2, 13.8, 13.5. Calculated: C=46.56%, N=27.17%, H=10.75% Found: C=46.49%, N=26.29, H=11.20%

The above physico-chemical characteristics correspond to the structure:

EXAMPLE 1b

Preparation of Bis(diethylamino)bis(nitric Oxide) Adduct

In the high pressure method a Parr shaker was used. NO was added to the reservoir which makes it possible to fill the reaction vessel without opening it directly to the NO tank. The mixture of diethylamine (100 ml) and diethyl ether (100 ml) was added to the reaction vessel. The reaction vessel was cooled to −78° C. and subjected to several evacuation/nitrogen flush cycles to remove as much of the oxygen as possible. NO was then introduced at a pressure of about 100 psi. The reaction vessel was allowed to slowly warm to room temperature overnight (18 hr), with shaking. The excess NO was flushed off with $N_2$ and the product was filtered and washed with diethyl ether. The crude yield was 5 grams. Purification and analysis were the same as in Example 1a.

EXAMPLE 2

Preparation of Bis(piperidine)bis(nitric Oxide) Adduct

To conduct this preparation, the Parr apparatus was modified by remounting the bottle clamp such that stirring with a magnetic stirrer was possible. Yields are thus greatly improved.

A solution of 50.0 ml piperidine (0.506 mol) in 150 ml ether was deoxygenated for 5 minutes with nitrogen and placed in the Parr holder. The solution was stirred vigorously, cooled in a large dry ice bath and NO admitted to a pressure of 75 psig. Both dry ice and NO were replenished for the next 4 hours and then the reaction was left to slowly approach room temperature overnight. After 16 hours, the NO pressure at room temperature was 70 psig and this was vented. The slurry was flushed with nitrogen and filtered. The white solid was washed with ether and dried in vacuo for 3 hours to afford 42.7 g of crystalline colorless product, m.p. 78°–79° C. dec., yield 73%. $^1$H NMR ($D_2O$) 1.4–1.6 (m, 2H), 1.6–1.8 (m, 10H), 3.06 (t, 4H, J=5.6 Hz), 3.15 (t, 4H, J=5.5 Hz). $^{13}$C NMR ($D_2O$) 24.50, 25.23 (2C), 25.36, 27.44 (2C), 47.41 (2C), 55.84 (2C).

The above physico-chemical characteristics correspond to the structure:

EXAMPLE 3

Preparation of Bis(morpholino)bis(nitric Oxide) Adduct

This material was prepared utilizing the methodology herein disclosed to prepare other compounds encompassed by the present invention (e.g., Example 2) by reacting morpholine with nitric oxide. The prepared compound exhibited the following $^1$H NMR spectrum:

2.7–2.9 (m, 4H), 3.1–3.2 (m, 4H), 3.6–3.8 (m, 4H), 3.9–4.0 (m, 4H); and ultraviolet spectrum: $\lambda_{max}$ ($\epsilon$) 252 nm ($8.8\times10^3 M^{-1} cm^{-1}$).

The above physico-chemical characteristics correspond to the structure:

EXAMPLE 4

Preparation of Bis(pyrrolidino)bis(nitric Oxide) Adduct

The title compound is prepared by substituting pyrrolidine for piperidine in the preparation recited in Example 2. The compound of Formula I which is produced possesses the following formula:

EXAMPLE 5

Utilizing the procedure set forth in Example 2, and substituting the following nitrogen-containing heterocyclics for piperidine:
(a) azetidine,
(b) azacylooctane,
(c) 2-methylpiperidine,
(d) 3-methylpiperidine,
(e) 4-methylpiperidine,
(f) 2-ethylpiperidine,
(g) 4-phenylpiperidine,
(h) 2-propylpiperidine,
(i) 4-propylpiperidine,
(j) 4-tert.butylpiperidine,
(k) 2-methylpyrrolidine,
(l) 3-methylpyrrolidine,
(m) 1,2,3,6-tetrahydropyridine,
(n) 3-pyrroline,
(o) hexamethyleneimine,
(p) 1-aza-12-crown-4,
(q) 1-aza-15-crown-5, and
(r) 1-aza-18-crown-6 there are obtained the following Formula I compounds:
(a) bis (azetidine) bis (nitric oxide) adduct,
(b) bis (azacyclooctane) bis (nitric oxide) adduct,
(c) bis (2-methylpiperidine) bis (nitric oxide) adduct,
(d) bis (3-methylpiperidine) bis (nitric oxide) adduct,
(e) bis (4-methylpiperidine) bis (nitric oxide) adduct,
(f) bis (2-ethylpiperidine) bis (nitric oxide) adduct,
(g) bis (4-phenylpiperidine) bis (nitric oxide) adduct,
(h) bis (2-propylpiperidine) bis (nitric oxide) adduct,
(i) bis (4-propylpiperidine) bis (nitric oxide) adduct,
(j) bis (4-tert.butylpiperidine) bis (nitric oxide) adduct,
(k) bis (2-methylpyrrolidine) bis (nitric oxide) adduct,
(l) bis (3-methylpyrrolidine) bis (nitric oxide) adduct,
(m) bis (1,2,3,6-tetrahydropyridine) bis (nitric oxide) adduct,
(n) bis (3-pyrroline) bis (nitric oxide) adduct,
(o) bis (hexamethyleneimine) bis (nitric oxide) adduct,
(p) bis (1-aza-12-crown-4) bis (nitric oxide) adduct,
(q) bis (1-aza-15-crown-5) bis (nitric oxide) adduct, and
(r) bis (1-aza-18-crown-6) bis (nitric oxide) adduct.

The other secondary amine-NO complexes encompassed hereby are made using the same methods as used in Examples 1a to 5, the only principal difference being the identity of the starting secondary amines. The product made in each case has the formula $R_1R_2NN_2O_2^- R_1R_2H_2N^+$. The synthesis of the salts containing the other cations is done by conventional methods, most particularly by a metathesis reaction, a method well known to one of ordinary skill in the art. (See Drago et al.) To make the sodium salt of the compound produced in example 1, the diethylammonium salt is dissolved in ethyl alcohol and reacted with sodium ethoxide according to the following reaction:

$$R_1R_2NN_2O_2^- R_1R_2H_2N^+ + NaOEt \rightarrow EtOH + R_1R_2NH + R_1R_2NN_2O_2^- Na^+.$$

The product is precipitated by flooding the reaction mixture with ether and then washed with neutralized chloroform. The other salts can be made by similar metathesis reactions.

Pharmacological Properties

Pharmacology Experiment I

The effect on the mean arterial blood pressure and heart rate of male Sprague-Dawley rats of a composition of the present invention containing the compound of Example 1 was measured using a standard technique. A pressure transducer (Bell and Howell, type 4-327-I) was connected to the right carotid artery via a catheter containing heparinized saline. The mean arterial pressure and heart rate were recorded on a Gould (Model 2800) 8-channel recorder. The rats were anesthetized with nembutal at an initial dose of 35 mg/kg body weight and recurrent smaller injections as needed. The compounds were dissolved in a pharmaceutical carrier and injected into the rats via a catheter in the right femoral vein. Table 1 shows the results obtained.

TABLE 1

| Compound | Dose (μmole/kg) | Mean Arterial Pressure | | | Heart Rate | |
|---|---|---|---|---|---|---|
| | | Initial (mm Hg) | Post (mm Hg) | Change | Initial (beats/min) | Post (beats/min) |
| $(Et)_2NN_2O_2$ $(Et)_2H_2^+$ | 3.90 | 102 | 36 | −66 | 480 | 480 |
| SNP | 0.34 | 113 | 56 | −57 | 403 | 454 |

TABLE 1-continued

| Compound | Dose (μmole/kg) | Mean Arterial Pressure | | | Heart Rate | |
| | | Initial | Post (mm Hg) | Change | Initial | Post (beats/min) |
|---|---|---|---|---|---|---|
| NaNO$_2$ | 4.00 | 126 | 48 | −78 | 360 | 420 |
| NaNO$_3$ | 42.00 | 117 | 120 | 3 | 420 | 420 |

In Table 1, the pharmaceutical carrier was Abbott's 5% dextrose USP. SNP, NaNO$_2$, and NaNO$_3$ were used as controls. SNP and NaNO$_2$ are known vasodilators, NaNO$_3$ is the oxidative breakdown product of NaNO$_2$ and has little vasodilatory effect. The results show that $(Et)_2NN_2O_2^-$ $(Et)_2H_2N^+$ is a potent anti-hypertensive, decreasing the blood pressure significantly. The peak value of the blood pressure decrease, shown in Table 1, takes only about 30 seconds to 1 minute to occur, after injection, and the blood pressure starts to rise again soon after and has totally recovered within 10 to 15 minutes.

Pharmacology Experiment II

The vasorelaxant activities of secondary heterocyclic amine-nitric oxide complexes was tested.

Figure 1:
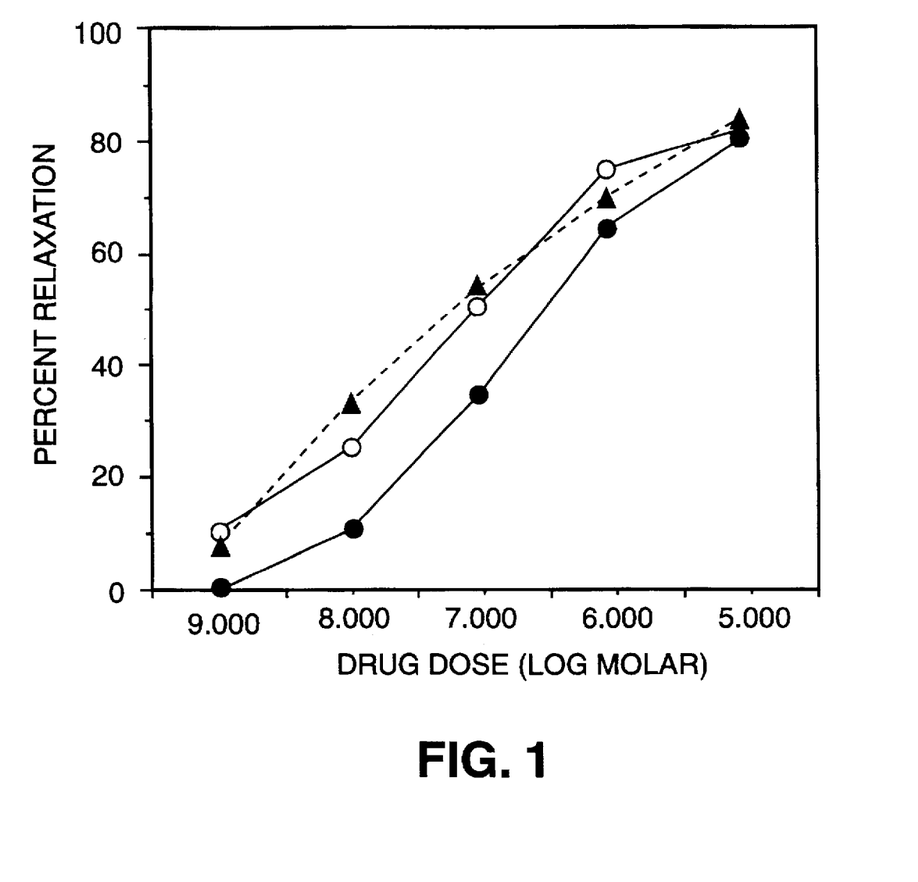
FIG. 1. Dose response curve obtained in Pharmacology Experiment II, below, wherein the bis(piperidino)bis(nitric oxide) Adduct of Example 2 was tested for vasorelaxant activity by utilizing a standard isolated vascular ring preparation.
Figure 2:
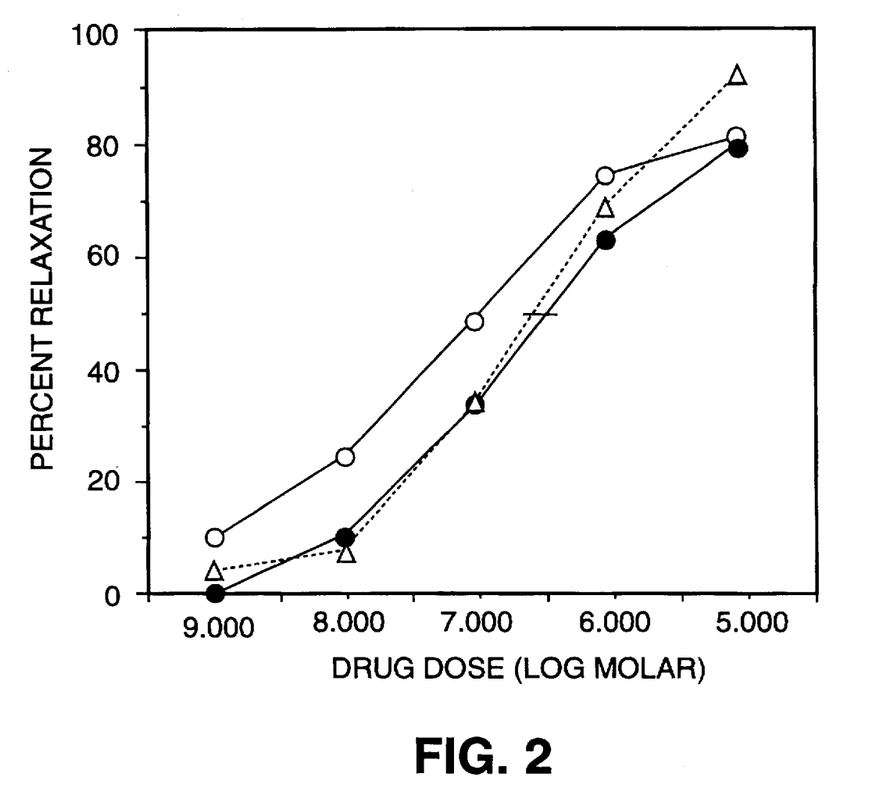
FIG. 2. Dose response curve obtained in Pharmacology Experiment II, below, wherein the bis(morpholino)bis(nitric oxide) Adduct of Example 3 was tested for vasorelaxant activity by utilizing a standard isolated vascular ring preparation.

A standard isolated vascular ring preparation was used to establish the potencies of the compounds of Examples 2 and 3, described above. In the test procedures utilized, thoracic aortic rings from New Zealand White rabbits were suspended in pH 7.4 buffer at 37° C. and a 10 g preload was applied to each. After equilibration for 2 hours, the rings were preconstricted with norepinephrine. By measuring the grams of relaxation induced by adding the complexes to the organ baths at successively increasing concentrations from $10^{-9}$ to 10–5M, a dose-response curve was constructed for each compound as shown in FIGS. 1 and 2. The piperidine derivative (Example 2, FIG. 1) was at least as potent as the clinically used positive controls, sodium nitroprusside and glyceryl trinitrate, while the morpholine analogue (Example 3, FIG. 2) also had an EC$_{50}$ (concentration required to induce 50% relaxation) in the submicromolar range.

Pharmacology Experiment III

Each of the following compounds:
(a) bis (azetidine) bis (nitric oxide), adduct,
(b) bis (azacyclooctane) bis (nitric oxide) adduct,
(c) bis (2-methylpiperidine) bis (nitric oxide) adduct,
(d) bis (3-methylpiperidine) bis (nitric oxide) adduct,
(e) bis (4-methylpiperidine) bis (nitric oxide) adduct,
(f) bis (2-ethylpiperidine) bis (nitric oxide) adduct,
(g) bis (4-phenylpiperidine) bis (nitric oxide) adduct,
(h) bis (2-propylpiperidine) bis (nitric oxide) adduct,
(i) bis (4-propylpiperidine) bis (nitric oxide) adduct,
(j) bis (4-tert.butylpiperidine) bis (nitric oxide) adduct,
(k) bis (2-methylpyrrolidine) bis (nitric oxide) adduct,
(l) bis (3-methylpyrrolidine) bis (nitric oxide) adduct,
(m) bis (1,2,3,6-tetrahydropyridine) bis (nitric oxide) adduct,
(n) bis (3-pyrroline) bis (nitric oxide) adduct,
(o) bis (hexamethyleneimine) bis (nitric oxide) adduct,
(p) bis (1-aza-12-crown-4) bis (nitric oxide) adduct,
(q) bis (1-aza-15-crown-5) bis (nitric oxide) adduct and
(r) bis (1-aza-18-crown-6) bis (nitric oxide) adduct,
is tested for cardiovascular properties utilizing the procedures set forth in the above Experiments I and II; each of the compounds (a) to (r) is expected to possess cardiovascular properties in mammals, and to be useful in the present inventive methods and pharmaceutical compositions.

Pharmaceutical Compositions

The compositions of this invention are useful for treating any cardiovascular disorder that will respond favorably to a decrease in blood pressure. These disorders include chronic hypertension, hypertensive crisis (an acute hypertensive emergency), acute congestive heart failure, angina, acute myocardial infarction, left ventricular failure, cerebrovascular insufficiency and intracranial haemorrhage. Because of the fast response upon intravenous injection the compositions are particularly advantageous for treating acute disorders such as hypertensive crisis, toxemia of pregnancy and acute congestive heart failure. The preferred method of administration is by injection into the blood system, most preferably by intravenous injection. The chronic disorders can be treated by continuous intravenous infusion. A suitable dosage for intravenous administration is about 0.01 to 10.0 mg/kg per day.

The pharmaceutical compositions of the invention are comprised of the compounds of Formula I and a pharmaceutical carrier. The carrier can be any of those conventionally used and is limited only by chemico-physical considerations such as solubility and lack of reactivity with the compound and by the route of administration. For intravenous administration, the carrier will be aqueous and may contain solubilizing agents, buffers, preservatives, antioxidants, chelating agents, and agents to control the tonicity, such as dextrose or sodium chloride. The requirements for effective pharmaceutical carriers for injectable compositions are well known by one of ordinary skill in this art. (See "Pharmaceutics and Pharmacy Practice", J.B. Lippincott Company, Philadelphia, 1982, edited by Banker and Chalmers, pages 238–250, which are incorporated by reference, also see ASHP "Handbook on Injectable Drugs" 4th edition by Trissel, pages 622–630, which lists commercially available intravenous infusion solutions, these pages are incorporated by reference.) The compounds may also be formulated as inclusion complexes, such as, for example, cyclodextrin inclusion complexes; or the compounds may be carried within liposomes. Preferred pharmaceutical carriers for injection are PBS (phosphate buffered saline), 5% dextrose and sterile water. Since the compounds of formula I are subject to being oxidized by oxygen, an antioxidant, such as ascorbate, can be added to the carrier to increase the shelf-life.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Each of the publications and patents referred herein above are expressly incorporated herein by reference in their entirety.

What is claimed is:

1. A pharmaceutical composition comprising a compound of formula (I):

wherein R$_1$ and R$_2$ together with the nitrogen they are bonded to form a heterocyclic ring of the formula wherein z is 2 to 5; $M^{+x}$ is a pharmaceutically acceptable cation; and x is the valence of the cation; and a pharmaceutically acceptable carrier.

2. The composition of claim 1, wherein $R_1$ and $R_2$, together with the nitrogen they are bonded to, form a heterocyclic ring selected from the group consisting of 1-aza-12-crown-4, 1-aza-15-crown-5, and 1-aza-18-crown-6.

3. The composition of claim 1, wherein $M^{+x}$ is selected from the group consisting of a group I ion, a group II ion and $NR_3R_4R_5R_6^+$, wherein $R_3$, $R_4$, $R_5$ and $R_6$ are selected from the group consisting of H, $C_1$–$C_{12}$ alkyl, $C_3$–$C_7$ cycloalkyl and benzyl.

4. The composition of claim 1, wherein $M^{+x}$ is $Na^+$, $Ca^{+2}$, $Mg^{+2}$ or $(R_1)(R_2)NH_2^+$.

* * * * *

UNITED STATES PATENT AND TRADEMARK OFFICE
CERTIFICATE OF CORRECTION

PATENT NO. : 5,731,305
DATED : March 24, 1998
INVENTOR(S) : Keefer, et al.

It is certified that error appears in the above-identified patent and that said Letters Patent is hereby corrected as shown below:

IN THE TITLE PAGE:

Please add the following statement:

-- [*] Notice: This patent is subject to a terminal disclaimer. --

Signed and Sealed this

Seventeenth Day of April, 2001

Attest:

NICHOLAS P. GODICI

Attesting Officer

Acting Director of the United States Patent and Trademark Office